US005886199A

United States Patent [19]
Ito et al.

[11] Patent Number: 5,886,199
[45] Date of Patent: Mar. 23, 1999

[54] PROCESS FOR PRODUCING 3-CHLOROMETHYL-3-ALKYLOXETANES

[75] Inventors: Naokazu Ito; Toshiro Hirose, both of Aichi, Japan

[73] Assignee: Toagosei Co., Ltd., Tokyo, Japan

[21] Appl. No.: 10,508

[22] Filed: Jan. 22, 1998

[30] Foreign Application Priority Data

Jan. 24, 1997 [JP] Japan .................................. 9-024563
Jan. 31, 1997 [JP] Japan .................................. 9-031384
Jul. 7, 1997 [JP] Japan .................................. 9-196450

[51] Int. Cl.$^6$ .................................................. C07D 305/00
[52] U.S. Cl. ............................................................ 549/511
[58] Field of Search ............................................. 549/511

[56] References Cited

U.S. PATENT DOCUMENTS 5,703,194  2/1998  Malik et al. ............................ 549/511

FOREIGN PATENT DOCUMENTS 39-10342  6/1964  Japan .

OTHER PUBLICATIONS

Tsukamoto, A et al., "Poly(vinyl chloride) compositions" CA80: 84266, 1984.
Miura et al., "3–Chloromethyl–3–Ethyloxacyclobutane," Chemical Abstracts, vol. 61, 11971–11972 (1964).
Petrova et al., "Synthesis of Oxacyclobutane Derivatives from the Trihydric Alcohols, Methyltrimethyolomethane," Chemical Abstracts, vol. 64, 14153–14154 (1966).

*Primary Examiner*—Amelia A. Owens
*Attorney, Agent, or Firm*—Heslin & Rothenberg, P.C.

The present invention is to provide for a process for producing 3-chloromethyl-3-alkyloxetanes from a 1,1-bis(chloromethyl)-1-hydroxymethylalkane or its carboxylate ester through a dehydrogen chloride reaction or a deacid chloride reaction in an aqueous solution or suspension of an alkaline compound. The reaction is conducted, either in the presence of a phase transfer catalyst or an anion exchange resin having an ammonium group, or, while distilling the formed 3-chloromethyl-3-alkyloxetane out azeotropically with water. The invention enables one to produce 3-chloromethyl-3-alkyloxetanes within a shorter period of time and with a higher yield, and thus the process is much advantageous and useful from the industrial points of view.

5 Claims, No Drawings

PROCESS FOR PRODUCING 3-CHLOROMETHYL-3-ALKYLOXETANES

BACKGROUND OF THE INVENTION

1. Field of the Invention

The present invention relates to a process for producing 3-chloromethyl-3-alkyloxetanes (referred to as "OXCs", hereinafter). OXCs are oxetane compounds which are capable of being ring-openingly polymerized by themself. Besides, they are useful compounds as intermediates for the production of various oxetane compounds. Thus, the invention belongs to a manufacturing art for chemicals.

2. Description of the Prior Art

As for the production of OXCs, a process has been known, in which 1,1-bis(choloromethyl)-1-hydroxymethylpropane or its acetate ester is allowed to react with potassium hydroxide in an alcoholic solvent which may optionally be diluted with water, followed by filtering the isolated inorganic salt off, evaporating the solvent, and vacuum distillation to give 3-choromethyl-3-ethyloxetane. Also, a process has been known, in which the above reaction product is mixed with water to dissolve the inorganic salt, and the mixture is extracted with an organic solvent, followed by evaporation of the organic solvent and vacuum distillation to give 3-chloromethyl-3-ethyloxetane. According to the description of Japanese Patent Publication No. 10342/1964, 3-chloromethyl-3-ethyloxetane can be produced by these processes in 40% to 80% yield.

These processes, however, necessitate a step of filtering the inorganic salt off, or extraction with an organic solvent to obtain the objective product, and also necessitate a step of recovering the alcohol used as the reaction solvent, as well as a step of removing the water formed in the reaction for reuse. Thus, such prior processes are not satisfactory from the commercial points of view.

While, in a process in which the reaction is effected in an aqueous alkali solution, without using any alcoholic solvent, there is no necessity of recovering the alcohol, but this process has some problems in a lower reaction rate as compared with a reaction in an alcoholic solvent, and in needing much more reaction time for a sufficient conversion of the starting material, as well as a lower OXC selectivity.

SUMMARY OF THE INVENTION

An object of the present invention is to provide for a commercially advantageous process for producing OXCs within a shorter reaction period of time and with a higher yield, by overcoming the problems involved in the prior art.

After extensive investigations to solve these problems, the present inventors have found that, in the process for producing an OXC from a 1,1-bis(chloromethyl)-1-hydroxymethylalkane or its carboxylate ester through dehydrogen chloride or deacid chloride reaction, the OXC can be produced within a shorter period of time and with a higher yield, if the reaction is conducted in an aqueous solution or suspension of an alkaline compound, either in the presence of a phase transfer catalyst or an anion exchange resin having an ammonium group, or, while distilling the formed OXC out azeotropically with water, and thus they have accomplished the present invention.

Accordingly, the present invention relates to a process for producing OXCs, which is characterized by that, in the production of an OXC from a 1,1-bis(chloromethyl)-1-hydroxymethylalkane or its carboxylate ester through a dehydrogen chloride or deacid chloride reaction, the reaction is carried out in an aqueous solution or suspension of an alkaline compound, either in the presence of a phase transfer catalyst or an anion exchange resin having an ammonium group, or, while distilling the formed OXC out azeotropically with water. 1,1-Bis(chloromethyl)-1-hydroxymethylalkanes used in the present invention may readily be obtained by chlorinating a trimethylolalkane with hydrogen chloride or others, in particular, in the presence of, for example, 0.01 to 0.2 mole of a lower ($C_2$ to $C_5$) aliphatic carboxylic acid, such as acetic and propionic acids, per mole of the trimethylolalkane, if desired, using an organic compound other than alcohols and esters, which forms an azeotropic mixture with water, as the reaction solvent, whereby water formed is distilled out of the reaction system during the reaction. In the present invention, 1,1-bis (chloromethyl)-1-hydroxymethylethane and 1,1-bis (chloromethyl)-1-hydroxymethylpropane are preferred because of their availability and easy technical handling. Carboxylate esters, such as acetate, propionate, butyrate and benzoate esters, of 1,1-bis(chloromethyl)-1-hydroxymethylalkanes may be used as the starting material, among which acetate and propionate esters are preferred because of the availability and easy technical handling.

The aqueous solution or suspension of an alkaline compound, used in the present invention, may be prepared by dissolving or suspending an alkali metal hydroxide or the like in water. As the alkaline compound used, sodium hydroxide, potassium hydroxide, lithium hydroxide, calcium hydroxide, sodium carbonate, sodium hydrogencarbonate, etc. are illustrated. Among them, sodium hydroxide and potassium hydroxide are preferred because they secure sufficient conversion of the starting material within a shorter period of time. Suitable amount of the alkaline compound used is within the range from 1 to 2 moles per mole of the starting material, when a 1,1-bis (chloromethyl)- 1-hydroxymethylalkane is used, or within the range from 2 to 3 moles per mole of the starting material, when its carboxylate ester is used. The concentration of an alkaline compound in the aqueous solution or suspension of an alkaline compound is preferably 1% to 60% by weight, more preferably 5% to 25% by weight.

In the present invention, any of the known phase transfer catalysts (for example, those disclosed in "SOKAN IDO SHOKUBAI [Phase Transfer Catalysts in organic Synthesis]", co-authored by W. P. Weber and G. W. Gokel, co-translated by Iwao TABUSHI and Takako NISHITANI, and published from K. K. KAGAKU DOJIN) may be used, among which quaternary ammonium and phosphonium salts are preferred. Specifically, tetra-n-butylammonium bromide, tetra-n-butylammonium hydrogensulfate, benzyltriethylammonium chloride, trioctylmethylammonium chloride, tetra-n-butylphosphonium bromide, trioctylethylphosphonium chloride, and tetraphenylphosphonium chloride are illustrated.

Using amount of the phase transfer catalyst is preferably from 0.05% to 20% by weight, more preferably 0.1% to 10% by weight, based upon the amount of the 1,1-bis (chloromethyl)-1-hydroxymethylalkane or its carboxylate ester.

Anion exchange resins having an ammonium group used in the present invention are not definitely restricted, so far as they are insoluble in the aqueous alkaline compound solution or suspension and the starting material such as 1,1-bis (chloromethyl)-1-hydroxymethylalkane. For example, AMBERLYST A-26, manufactured by Organo Corp., and DIAION PA-306, manufactured by Mitsubishi chemical Corp., which are polystyrene resins having an ammonium group, are illustrated.

Amount of the anion exchange resin used is not specifically restricted, but it may freely be selected according to the kind of the starting materials, reaction temperatures, and the mode of reaction. To obtain an OXC with a high yield within a short period of time, use of the anion exchange resin in an amount of not less than 0.01% by weight based upon the amount of a 1,1-bis(chloromethyl)-1-hyroxymethylalkane or its carboxylate ester, is preferred. The anion exchange resin once used in the reaction can be separated and recovered from the reaction mixture through a simple procedure, such as filtration, and may be reused without any specific purification step.

While the phase transfer catalysts are soluble in an aqueous alkaline solution or suspension, so that any means is needed for the recovery and reuse of the catalyst, the anion exchange resins can readily be recovered and reused, thus, the latter being preferred in the present invention.

Production process according to the present invention is characteristic in that the reaction is carried out in an aqueous solution or suspension of an alkaline compound, either using a phase transfer catalyst or an anion exchange resin having an ammonium group as catalyst, or, while distilling the formed OXC out azeotropically with water. The way of distilling-out may be either continuous or in batch system, but the continuous distillation is desirable because of the easiness of control of the reaction operation.

The reaction can be carried out not only under the atmospheric pressure, but under a subatmospheric or super-atmospheric pressure. The reaction temperature is preferably within the range from 40° C. to 110° C., more preferably from 60° C. to 105° C., the most preferably from 65° C. to 85° C.

Reaction temperature of higher than 110° C. increases the formation of by-product, thus, lowering the yield. While, reaction temperature of lower than 40° C. lowers the reaction rate, thus lowering conversion of the starting material.

The reaction period of time may be determined depending on the material used, reaction temperature and the mode of reaction as mentioned later, but it should be determined in due consideration of conversion ratio in the reaction, while tracking the amount of the reaction materials through gas chromatography.

DESCRIPTION OF THE PREFERRED EMBODIMENTS

The present invention may be carried out in any mode of batch, semi-batch and continuous systems. Embodiments of the reaction will be shown below, which are, however, only for illustration, and not for limiting the mode of reaction.

(a) Batch system
(1) In a reactor are charged a 1,1-bis(chloromethyl)-1-hydroxymethylalkane or its carboxylate ester, an aqueous solution or suspension of an alkaline compound, and a phase transfer catalyst or an anion exchange resin having an ammonium group, and the mixture was allowed to react under heating and stirring. After the reaction is over, the reaction mixture is fractionated to give an organic layer and an inorganic layer. When the anion exchange resin is used, the resin has been removed before being fractionated. In this process, a water-insoluble, inert solvent may be used. Such inert solvents include toluene, xylene, hexane, chlorobenzene, methyl t-butyl ether, methyl isobutyl ketone, and the like.
(2) In a reactor are charged a 1,1-bis(chloromethyl)-1-hydroxymethylalkane or its carboxylate ester and an aqueous solution or suspension of an alkaline compound, and the reaction is continued under heating and stirring, while distilling the formed OXC out azeotropically with water, until distillation of the OXC is over. The cooled distillate is fractionated to give an organic layer containing an OXC and an aqueous layer. The reaction may be continued while returning the separated aqueous layer to the reactor. After the reaction, the aqueous alkaline solution or suspension containing an inorganic salt is discharged from the reactor.
(3) To a reactor are charged a 1,1-bis(chloromethyl)-1-hydroxymethylalkane or its carboxylate ester, an aqueous solution or suspension of an alkaline compound, and a phase transfer catalyst or an anion exchange resin having an ammonium group, and the mixture is treated in similar way as in (2).

(b) Continuous system
(1) From the top of a reaction column filled with an anion exchange resin are fed a 1,1-bis(chloromethyl)-1-hydroxymethylalkane or its carboxylate ester, and an aqueous solution or suspension of an alkaline compound, and the mixture is allowed to react under heating. The reaction mixture flown out of the bottom of the column is fractionated to give an organic layer and an aqueous layer.
(2) From the top of a reaction/distillation column having plates or packing are fed a 1,1-bis(chloromethyl)-1-hydroxymethylalkane or its carboxylate ester, and an aqueous solution or suspension of an alkaline compound. The mixture is allowed to react by blowing a steam vapor stream from the bottom, and distilling the formed OXC out azeotropically with water.
(3) From the top of a reaction/distillation column having plates or packing are fed a 1,1-bis(chloromethyl)-1-hydroxymethylalkane or its carboxylate ester, an aqueous solution or suspension of an alkaline compound, and a phase transfer catalyst. The mixture is allowed to react by blowing a steam vapor stream from the bottom, and distilling the formed OXC out azeotropically with water.

The distillate is cooled and fractionated to give an organic layer and an aqueous layer in similar way as in above (a). The separated aqueous layer may be reused. While, the aqueous alkaline solution or suspension containing an inorganic salt is discharged in a definite proportion from the bottom of the distillation column. In this procedure, an inert gas, such as nitrogen, may be incorporated in the steam vapor stream.

Process as mentioned in (a) may be conducted in a semi-batch system by continuously charging one of the starting materials, or in a continuous system by continuously charging both starting materials and the phase transfer catalyst or the anion exchange resin. At this time, the aqueous alkaline solution or suspension containing the inorganic salt is discharged out of the reactor, together with the phase transfer catalyst or the anion exchange resin in definite proportions. Further, the reaction may be conducted according to a combination of such procedures as mentioned above, for example, the reaction is allowed to proceed by heating and stirring as in the conventional way up to a certain extent, followed by the later procedures as illustrated in (a) or (b).

Anionic exchange resins which have been used in the reaction may be separated from the reaction mass, for example, by filtration, and reused in the following reaction.

OXCs can be obtained in a high purity from the OXC-containing organic layer resulting from the reaction, according to a purification procedure, such as distillation and/or chromatography, as used in the conventional procedure of organic synthesis.

The present invention will more specifically be described with reference to the following examples.

EXAMPLE FOR REFERENCE (Synthesis of 1,1-bis(chloromethyl)-1-hydroxymethylpropane)

In a 300 ml-volume four-necked flask were placed 1.0 mole of trimethylolpropane, 0.1 mole of glacial acetic acid, and 100 ml of m-xylene solvent. While being stirred by a magnetic stirrer, the mixture was refluxingly heated up to about 140° C. under an atmospheric pressure, and was fed with a hydrogen chloride gas stream at a 0.25 mole/hour rate to proceed the reaction. While keeping the refluxing state under stirring, and allowing the temperature to gradually elevate, water and m-xylene were distilled out, and the xylene layer, separated from the aqueous layer, was continuously returned to the reactor. After 21 hour reaction, the final reaction temperature had reached 170° C.

After the reaction, the reaction mass was subjected to gas choromatographic analysis (hereinafter referred to as "GC analysis"). The measurement showed 100% conversion of trimethylolpropane, 77% selectivity of 1,1-bis (chloromethyl)-1-hyroxymethylpropane, 14% selectivity of 1-mono(chloromethyl)-1,1-bis(hydroxymethylpropane), and 9% selectivity of their esters.

EXAMPLE 1

In a 500 ml-volume glass reactor were charged 51 g of 1,1-bis(chloromethyl)-1-hydroxymethylpropane (0.3 mole) (hereinafter referred to as "BCP") and 200 g of an aqueous 10% by weight solution of NaOH (0.5 mole as NaOH). The mixture was heated under atmospheric pressure while stirring until distillation was observed. The distillate cooled at a condenser was collected in a receiver. After 3 hour reaction, distillation of the organic matter was over. Temperature of the reaction mixture was from 102° C. to 104° C. The distillate was fractionated to yield 32 g of an organic layer and 112 g of an aqueous layer.

After the reaction, the contents of 3-chloromethyl-3-ethyloxetane (hereinafter referred to as "EOXC") and BCP in the separated organic layer were quantitated by GC analysis. Residue in the reactor was extracted with methylene chloride, and the BCP content was quantitated by GC analysis, thus, to give a BCP conversion, EOXC selectivity and the yield, with the results as shown in Table 1 below. BCP conversion, EOXC selectivity and the yield were calculated according to the following equations. All % are in mole basis.

The conversion of BCP (%)=(1−unreacted BCP÷charged BCP)×100

The selectivity of EOXC (%)=produced EOXC÷(charged BCP−unreacted BCP)×100

The yield of EOXC (%)=The conversion of BCP×The selectivity of EOXC)÷100

EXAMPLE 2

Reaction was conducted in similar way as in Example 1, except that 300 g of an aqueous 5% by weight NaOH solution (0.375 mole as NaOH) was used as the starting material, to obtain 34 g of an organic layer and 107 g of an aqueous layer. The products were analyzed as in Example 1, with the results as shown in Table 1.

EXAMPLE 3

Reaction was conducted in similar way as in Example 1, except that the reaction mixture was heated under a subatmospheric pressure of about 300 mmHg until the distillation was observed, and the reaction was continued for 4 hours, while returning the aqueous layer distillate to the reactor. The reaction yielded 36 g of an organic layer. Temperature of the reaction mixture was ranging from 78° C. to 80° C. The results are shown in Table 1.

EXAMPLE 4

The starting materials as in Example 1 were charged in a reactor, and the mixture was heated to 80° C. under atmospheric pressure, while stirring. The reaction was allowed to proceed for 6 hours, while keeping the temperature at 80° C. Then, the mixture was heated under atmospheric pressure until the distillation was observed. The distillate cooled by a condenser was collected in a receiver. The reaction was continued for 3 hours before the distillation of the organic matter is over. The temperature of the reaction mass at this time was ranging from 102° C. to 105° C. The distillate was fractionated to obtain 33 g of an organic layer and 71 g of an aqueous layer, with the analytical results as shown in Table 1.

EXAMPLE 5

Reaction was conducted in similar way as in Example 1, except that 40 g of BCP acetate ester (0.19 mole) was used as the starting material. After 3 hour reaction, 19 g of an organic layer and 67 g of an aqueous layer were obtained with the analytical results as shown in Table 1.

EXAMPLE 6

Reaction was conducted in similar way as in Example 1, except that 47 g of 1,1-bis(chloromethyl)-1-hydroxymethylethane (0.3 mol) (hereinafter referred to as "BCE") was used as the starting material, thereby to give 30 g of an organic layer and 101 g of an aqueous layer. After the reaction, the products were analyzed to quantitate 3-chloromethyl-3-methyloxetane (hereinafter referred to as "MOXC") and the BCE material, and the BCE conversion, MOXC selectivity and the yield were calculated, with the results as shown in Table 1.

COMPARATIVE EXAMPLE 1

To a 500 ml-volume glass reactor were charged 51 g of BCP (0.3 mole) and 200 g of an aqueous 10% by weight NaOH solution (0.5 mole as NaOH). The reaction was allowed to proceed for 6 hours under stirring and refluxing. The temperature of the reaction mixture was ranging from 99° C. to 100° C. After the reaction, the reaction mass was cooled and fractionated to give an organic layer and an aqueous layer. The contents of EOXC and BCP in the organic layer was analyzed by GC analysis. After extracting the aqueous layer with methylene chloride, the contents of EOXC and BCP in the second organic layer were analyzed. BCP conversion, EOXC selectivity and the yield were calculated, with the results as shown in Table 1.

COMPARATIVE EXAMPLE 2

Reaction was conducted in similar way as in Comparative Example 1, except that the reaction was allowed to proceed for 6 hours at 80° C. without refluxing. Analyses as in Comparative Example 1 gave the results as shown in Table 1.

Comparative Example 3

Reaction was conducted in similar way as in Comparative Example 2, except that the reaction was allowed to proceed for 16 hours. Analyses as in Comparative Example 1 gave the results as shown in Table 1.

TABLE 1

|  | Reaction temp. (°C.) | Reaction time (hour) | BCP conversion (%) | OXC selectivity (%) | Yield (%) |
| --- | --- | --- | --- | --- | --- |
| Ex.1 | 100 | 3 | 99.9 | 80.9 | 81 |
| Ex.2 | 100 | 3 | 97.0 | 81.3 | 79 |
| Ex.3 | 80 | 4 | 94.1 | 87.8 | 83 |
| Ex.4 | 80 → 100 | 6 + 3 | 99.9 | 85.2 | 85 |
| Ex.5 | 100 | 3 | 99.9 | 80.1 | 80 |
| Ex.6 | 100 | 3 | 99.9 | 80.5 | 80 |
| Comp Ex.1 | 100 | 6 | 99.9 | 69.9 | 70 |
| Comp Ex.2 | 80 | 6 | 68.5 | 91.5 | 63 |
| Comp Ex.3 | 80 | 16 | 94.5 | 85.1 | 80 |

EXAMPLE 7

To a 500 ml-volume glass reactor were charged 51 g of BCP (0.3 mole), 200 g of an aqueous 10% by weight NaOH solution (0.5 mole as NaOH) and 2.5 g of tetra-n-butylammonium bromide (hereinafter referred to as "TBAB"). The reaction was allowed to proceed for 3 hours by heating up to 80° C. under atmospheric pressure, while stirring. After the reaction, the reaction mass was fractionated to give 36.4 g of an organic layer and an aqueous layer.

Results of the analyses as in Example 1 are shown in Table 2.

EXAMPLE 8

To a 500 ml-volume glass reactor were charged 51 g of BCP (0.3 mole), 150 g of an aqueous 10% by weight NaOH solution (0.38 mole as NaOH) and 1.0 g of TBAB. The reaction was allowed to proceed by heating the mixture under atmospheric pressure until the distillation was observed, while stirring, and continued for 3 hours until distillation of the organic matter was over. The temperature of the reaction mass was from 102° C. to 105° C. Cooled distillate was fractionated to give 33.3 g of an organic layer and 81.4 g of an aqueous layer, with the analytical results as shown in Table 2.

EXAMPLE 9

Reaction was conducted in similar way as in Example 7, except that the mixture was allowed to react at a temperature of 60° C. for 8 hours, thereby to obtain 39.0 g of an organic layer. The analytical results are shown in Table 2.

EXAMPLE 10

Reaction was conducted in similar way as in Example 7, except that 40 g of BCP acetate ester (0.19 mole)(hereinafter referred to as "BCPE") and 95 g of an aqueous 20% by weight NaOH solution (0.48 mole as NaOH) were used. After 3 hour reaction, 22.9 g of an organic layer was obtained. The analytical results are shown in Table 2.

EXAMPLE 11

Reaction was conducted in similar way as in Example 7, except that 47 g of BCE and 400 g of an aqueous 5% by weight NaOH solution (0.5 mole as NaOH) were used. After 3 hour reaction, 33.0 g of an organic layer was obtained. The analytical results are shown in Table 2.

EXAMPLE 12

Reaction was conducted in similar way as in Example 7, except that 150 g of an aqueous 10% by weight NaOH solution (0.38 mole as NaOH) and 0.5 g of TBAB were used. After 8 hour reaction, 38.5 g of an organic layer was obtained. The analytical results are shown in Table 2.

EXAMPLE 13

Reaction was conducted in similar way as in Example 12, except that 0.5 g of tetra-n-butylphosphonium bromide (hereinafter referred to as "TBPB") was used as the phase transfer catalyst. After 8 hour reaction, 38.0 g of an organic layer was obtained. The analytical results are shown in Table 2.

EXAMPLE 14

Reaction was conducted in similar way as in Example 12, except that 0.5 g of trioctylmethylammonium chloride (hereinafter referred to as "TOMAC") was used as the phase transfer catalyst. After 8 hour reaction, 38.4 g of an organic layer was obtained. The analytical results are shown in Table 2.

TABLE 2

|  | Material | Kind of catalysts | Amount[a] of catalyst (wt %) | Aqueous NaOH solution (wt %) | Amount[b] of NaOH (mole ratio) | Reaction temp. (C.°) | Reaction time (hr) | BCPs conversion (%) | OXCs selectivity (%) | Yield (%) |
| --- | --- | --- | --- | --- | --- | --- | --- | --- | --- | --- |
| Example 7 | BCP | TBAB | 5 | 10 | 1.67 | 80 | 3 | 99.7 | 91.8 | 92 |
| Example 8 | BCP | TBAB | 2 | 10 | 1.25 | 100 | 3 | 99.9 | 86.9 | 87 |
| Example 9 | BCP | TBAB | 5 | 10 | 1.67 | 60 | 8 | 91.0 | 94.5 | 86 |
| Example 10 | BCPE | TBAB | 5 | 20 | 2.50 | 80 | 3 | 99.9 | 90.1 | 90 |
| Example 11 | BCE | TBAB | 5 | 5 | 1.67 | 80 | 3 | 99.6 | 90.5 | 90 |
| Example 12 | BCP | TBAB | 1 | 10 | 1.25 | 80 | 8 | 94.8 | 90.0 | 85 |
| Example 13 | BCP | TBAB | 1 | 10 | 1.25 | 80 | 8 | 95.3 | 91.5 | 87 |
| Example 14 | BCP | TOMAC | 1 | 10 | 1.25 | 80 | 8 | 93.6 | 91.0 | 85 |

[a] The weight ratio of catalyst to materials
[b] The mole ratio of NaOH to materials

EXAMPLE 15

To a 500 ml-volume glass reactor were charged 51 g of BCP (0.3 mole), 75 g of an aqueous 20% by weight NaOH solution (0.38 mole as NaOH) and 40 g of AMBERLYST A-26 (an anion exchange resin) manufactured by Organo Corp. The mixture was heated to 80° C. and allowed to react for 8 hours under stirring. After the reaction, 100 ml of methylene chloride was added to the reaction mixture, and the ion exchange resin was filtered off. The reaction mass was fractionated to give an organic layer and an aqueous layer.

Contents of EOXC and BCP in the organic layer were quantitated by GC analysis, and BCP conversion and EOXC selectivity were calculated. The results are shown in Table 3.

EXAMPLE 16

The reaction was conducted in similar way as in Example 15, except that the anion exchange resin used and recovered in Example 15 was used. After 8 hour reaction, the products were analyzed, with the results as shown in Table 3.

10% by weight NaOH solution (0.38 mole as NaOH) were used. After 8 hour reaction, the products were analyzed, with the results as shown in Table 3.

TABLE 3

|  | Material | Anion exchange resins | Amount[a] of anion exchange resin | Aqueous NaOH solution (wt %) | Amount[b] of NaOH (mole ratio) | Reaction temp. (°C.) | Reaction time (hr) | BCPs conversion (%) | OXCs selectivity (%) | OXCs yield (%) |
|---|---|---|---|---|---|---|---|---|---|---|
| Example 15 | BCP | AMBERLYST A-26 | 80 | 20 | 1.25 | 80 | 8 | 94.0 | 93.2 | 87.6 |
| Example 16 | BCP | reuse from Exam. 1 | 80 | 20 | 1.25 | 80 | 8 | 93.7 | 92.1 | 86.3 |
| Example 17 | BCP | AMBERLYST A-27 | 60 | 10 | 1.50 | 100 | 3 | 99.5 | 83.9 | 83.5 |
| Example 18 | BCP | AMBERLITE IRA-401 | 80 | 10 | 1.25 | 80 | 8 | 93.2 | 90.6 | 84.4 |
| Example 19 | BCPE | AMBERLYST A-26 | 40 | 20 | 1.25 | 80 | 8 | 93.0 | 91.8 | 85.4 |
| Example 20 | BCE | AMBERLYST A-27 | 80 | 10 | 1.25 | 80 | 8 | 94.1 | 91.5 | 86.1 |

[a] The weight ratio of anion exchange resin to materials (100)
[b] The mole ratio of NaOH to materials

EXAMPLE 17

To a 500 ml-volume glass reactor were charged 51 g of BCP (0.30 mole), 180 g of an aqueous 10% by weight NaOH solution (0.45 mole as NaOH) and 30 g of AMBERLYST A-27 (an anion exchange resin) manufactured by Organo Corp. The mixture was heated under atmospheric pressure until the distillation was observed. The distillate cooled in a condenser was collected in a receiver. The reaction was continued for 3 hours until the distillation of the organic matter was over. Temperature of the reaction mass was from 102° C. to 105° C. The distillate was fractionated to give 35.6 g of an organic layer and 79.1 g of an aqueous layer. Contents of EOXC and BCP in the organic layer, as well as the content of BCP in the residue in the reactor, were analyzed, and BCP conversion and EOXC selectivity were calculated, with the results as shown in Table 3.

EXAMPLE 18

Reaction was conducted in similar way as in Example 15, except that 150 g of an aqueous 10% by weight of NaOH solution (0.38 mole as NaOH) was used, and the anion exchange resin used was AMBERLITE IRA-401 manufactured by Organo Corp. After 8 hour reaction, the products were analyzed, with the results as shown in Table 3.

EXAMPLE 19

Reaction was conducted in similar way as in Example 15, except that 40 g of BCPE (0.19 mole) and 95 g of an aqueous 20% by weight NaOH solution (0.48 mole as NaOH) were used. After 8 hour reaction, the products were analyzed, with the results as shown in Table 3.

EXAMPLE 20

Reaction was conducted in similar way as in Example 15, except that 47 g of BCE (0.3 mole) and 150 g of an aqueous As described herein, the present invention enables one to produce 3-chloromethyl-3-alkyloxetanes within a shorter period of time and with a higher yield, using a 1,1-bis (chloromethyl)-1-hyroxymethylalkane and/or its carboxylate ester and an aqueous solution or suspension of an alkaline compound as the starting materials. Thus, the present process is much advantageous and useful from the industrial points of view.

We claim:

1. A process for producing 3-chloromethyl-3-alkyloxetanes, which is characterized by that, in producing a 3-chloromethyl-3-alkyloxetane from a 1,1-bis (chloromethyl)-1-hydroxymethylalkane or its carboxylate ester through a dehydrogen chloride reaction or a deacid chloride reaction, the reaction is conducted in an aqueous solution or suspension of an alkaline compound, either in the presence of a phase transfer catalyst or an anion exchange resin having an ammonium group, or, while distilling the formed 3-chloromethyl-3-alkyloxetane out azeotropically with water.

2. A process according to claim 1, wherein the formed 3-chloromethyl-3-alkyloxetane is distilled out azeotropically with water, when the dehydrogen chloride reaction or the deacid chloride reaction is conducted in the presence of a phase transfer catalyst or an anion exchange resin having an ammonium group.

3. A process for producing 3-chloromethyl-3-alkyloxetanes according to claim 1 or 2, wherein the alkaline compound is sodium hydroxide or potassium hydroxide.

4. A process for producing 3-chloromethyl-3-alkyloxetanes according to claim 1 or 2, wherein the reaction temperature is from 40° C. to 110° C.

5. A process for producing 3-chloromethyl-3-alkyloxetanes according to claim 1, wherein the 1,1-bis (chloromethyl)-1-hydroxymethylalkane is 1,1-bis(chloromethyl)-1-hydroxymethylethane or 1,1-bis(chloromethyl)-1-hydroxymethylpropane.

* * * * *